(12) United States Patent
Cheong et al.

(10) Patent No.: US 8,900,582 B2
(45) Date of Patent: Dec. 2, 2014

(54) DEIMMUNIZED ANTI C-MET HUMANIZED ANTIBODIES AND USES THEREOF

(71) Applicant: Samsung Electronics Co., Ltd., Suwon-si (KR)

(72) Inventors: Kwang-ho Cheong, Seoul (KR); Seung-hyun Lee, Suwon-si (KR)

(73) Assignee: Samsung Electronics Co., Ltd., Suwon-Si (KR)

( * ) Notice: Subject to any disclaimer, the term of this patent is extended or adjusted under 35 U.S.C. 154(b) by 0 days.

(21) Appl. No.: 13/725,125

(22) Filed: Dec. 21, 2012

(65) Prior Publication Data
US 2013/0164281 A1 Jun. 27, 2013

(30) Foreign Application Priority Data
Dec. 22, 2011 (KR) ........................ 10-2011-0140399

(51) Int. Cl.
*A61K 39/395* (2006.01)
*C07K 16/28* (2006.01)

(52) U.S. Cl.
CPC ......... *C07K 16/2863* (2013.01); *C07K 2317/24* (2013.01); *C07K 2317/92* (2013.01)
USPC .................. 424/133.1; 424/155.1; 530/387.3; 530/387.7

(58) Field of Classification Search
None
See application file for complete search history.

(56) References Cited

U.S. PATENT DOCUMENTS

| 5,686,292 | A | 11/1997 | Schwall et al. |
| 6,214,344 | B1 | 4/2001 | Schwall et al. |
| 7,556,804 | B2 | 7/2009 | Prat |
| 7,892,550 | B2 | 2/2011 | Dennis et al. |
| 2006/0134104 | A1 | 6/2006 | Dennis et al. |
| 2011/0097262 | A1 | 4/2011 | Goetsch et al. |
| 2011/0104176 | A1 | 5/2011 | Cheong et al. |

FOREIGN PATENT DOCUMENTS

| EP | 1 997 511 A1 | 12/2008 |
| EP | 2 014 681 A1 | 1/2009 |
| KR | 1020080113218 A | 12/2008 |
| KR | 1020090013745 A | 2/2009 |
| KR | 1020110047698 A | 5/2011 |
| WO | WO 2010/064089 A1 | 6/2010 |
| WO | WO 2010/069765 A1 | 6/2010 |

OTHER PUBLICATIONS

Haigh et al, Oncology vol. 13 p. 1561 (1999).*
Bryson et al., "Prediction of Immunogenicity of Therapeutic Proteins", *Biodrugs*, 24 (1): 1-8 (2010).
Perry et al., "New Approaches to Prediction of Immune Responses to Therapeutic Proteins during Preclinical Development", *Drugs R D*, 9 (6): 385-396 (2008).

* cited by examiner

*Primary Examiner* — Sheela J Huff
(74) *Attorney, Agent, or Firm* — Leydig, Voit & Mayer, Ltd.

(57) ABSTRACT

A deimmunized anti c-Met humanized antibody and a pharmaceutical composition including the same, and method for the prevention and treatment of cancer.

12 Claims, 2 Drawing Sheets

DEIMMUNIZED ANTI C-MET HUMANIZED ANTIBODIES AND USES THEREOF

CROSS-REFERENCE TO RELATED APPLICATIONS

This application claims the benefit of Korean Patent Application No. 10-2011-0140399, filed on Dec. 22, 2011, in the Korean Intellectual Property Office, the disclosure of which is incorporated herein in its entirety by reference.

INCORPORATION-BY-REFERENCE OF MATERIAL SUBMITTED ELECTRONICALLY

Incorporated by reference in its entirety herein is a computer-readable nucleotide/amino acid sequence listing submitted concurrently herewith and identified as follows: One 17,650 Byte ASCII (Text) file named "711811_ST25.TXT," created on Dec. 21, 2012.

BACKGROUND

1. Field

The present disclosure relates to deimmuized anti c-Met humanized antibodies and pharmaceutical compositions including the same for the prevention or treatment of cancer.

2. Description of the Related Art c-Met is a receptor of a hepatocyte growth factor (HGF). HGF is a kind of cytokine that binds to an extracellular site of c-Met receptor tyrosine kinase to induce division, movement, cytomorphosis, and vasculogenesis of various normal cells and tumor cells. c-Met is a typical receptor tyrosine kinase present on a cell surface and is a cancer-causing gene, and in some cases, independently from the ligand HGF, c-Met is involved in various mechanisms related to tumors, including cancer development, cancer transition, movement of cancerous cells, invasion of cancerous cells, and neovasculogenesis. Thus, c-Met is gaining attention as an anti-cancer target.

In particular, overexpression of c-Met may contribute to the development of resistance to anti-cancer drugs, such as Erbitux™, Tarceva™, and Herceptin™ Erbitux™ and Tarceva™ are anti-cancer drugs that target EGFR (ERBB1) and act by blocking transmittance of signals associated with cancer generation mechanisms. Herceptin™ is a breast cancer drug that targets ERBB2 (HER2) and blocks transmittance of signals for the proliferation of cells. Accordingly, c-Met has become a target molecule for anti-cancer drugs.

The AbF46 antibody is an c-Met specific antibody generated through mouse immunization. This mouse-derived antibody may cause immunogenicity, such as an anti-isotypic reaction, when administered to humans for therapeutic purposes, so various antibody engineering technologies have been developed to prevent immunogenicity. Chimeric antibodies are manufactured by substituting a constant region that may cause an anti-isotypic reaction with a constant region of a human antibody through genetic engineering. Examples of chimeric antibodies manufactured using this antibody engineering method are Basiliximab™ (Simulect; IgG1 anti-CD25, Norvatis) and Cetuximab™ (Erbitux; IgG1 anti-EGFR, ImClone). However, clinical trial results showed the occurrence of a human anti-chimeric antibody reaction (HACA).

As described above, chimeric antibodies have been substantially improved compared to mouse antibodies in terms of anti-idiotypic reaction, but, mouse-derived amino acids are still present in variable regions and thus, side effects with respect to a potential anti-idiotypic reaction may occur. As an antibody engineering method for resolving this problem, a humanized antibody production technology has been developed. However, even when complementarity determining regions (CDR) are drafted on an optimized human antibody framework, an amino acid affecting antigen binding may be present on a mouse antibody framework, so that the antigen binding may not be preserved. Accordingly, an additional antibody engineering technology for restoring antigen binding is necessary. Among novel antibody medicines that are commercially available following the approval of the U.S. food and drug administration, humanized antibodies overwhelmingly dominate the market compared to mouse or chimeric antibodies, and Herceptin™ (Genentech), which is a breast cancer drug, shows a very low level of about 0.1% of anti-human antibody reaction in clinical trials.

Accordingly, there is a need to develop a humanized antibody of mouse anti c-Met antibody that has minimized immunogenicity and can enter previous-phase clinical trials.

SUMMARY

Provided are anti c-Met humanized antibodies that, in some embodiments, have reduced immunogenicity (deimmunized). An aspect of the present invention provides an anti c-Met humanized antibody including a heavy chain variable region comprising an amino acid sequence set forth in any of SEQ ID NO: 1 to SEQ ID NO: 5, and a light chain variable region comprising an amino acid sequence set forth in any of SEQ ID NO: 6 to SEQ ID NO: 9.

Also provided are pharmaceutical compositions and methods for the prevention or treatment of cancer using the anti c-Met humanized antibodies.

Additional aspects will be set forth in part in the description which follows and, in part, will be apparent from the description, or may be learned by practice of the presented embodiments.

BRIEF DESCRIPTION OF THE DRAWINGS

These and/or other aspects will become apparent and more readily appreciated from the following description of the embodiments, taken in conjunction with the accompanying drawings in which.

DETAILED DESCRIPTION

Reference will now be made in detail to embodiments, examples of which are illustrated in the accompanying drawings, wherein like reference numerals refer to like elements throughout. In this regard, the present embodiments may have different forms and should not be construed as being limited to the descriptions set forth herein. Accordingly, the embodiments are merely described below, by referring to the figures, to explain aspects of the present description. As used herein, the term "and/or" includes any and all combinations of one or more of the associated listed items. The term "c-Met" or "c-Met protein" refers to a receptor tyrosine kinase that binds to a hepatocyte growth factor. The c-Met or c-Met protein includes, for example, a polypeptide that is encoded by a nucleotide sequence provided to GenBank Accession Number NM_000245, a protein that is encoded by a polypeptide sequence provided to GenBank Accession Number NM_000236, or an extracellular domain thereof. The receptor tyrosine kinase c-Met is involved in various mechanisms, including cancer development, cancer transition, movement of cancerous cells, invasion of cancerous cells, and neovasculogenesis.

According to an embodiment of the present invention, the c-Met is derived from one selected from a human, a monkey, a mouse, and a rat.

An animal-derived antibody is produced by immunizing an animal with a desired antigen. In general, when the animal-derived antibody is administered to humans for therapeutic purposes, immunogenicity may arise. A chimeric antibody has been developed to prevent the occurrence of immunogenicity. The chimeric antibody is manufactured by substituting a constant region of an animal-derived antibody, which causes an anti-isotypic reaction, with a constant region of a human antibody through a generic engineering method. The chimeric antibody has been substantially improved compared to animal-derived antibodies in terms of an anti-isotypic reaction, but, still, mouse-derived amino acids are present in variable regions and thus, side effects with respect to a potential anti-idiotypic reaction may occur. A humanized antibody has been developed to improve such side effects. The humanized antibody is manufactured by grafting complementarity determining regions (CDR) of the chimeric antibody, which play an important role in binding of an antigen, on a human antibody framework.

Regarding the CDR grafting for producing a humanized antibody, it is the most important to select an optimized human antibody that may accept CDR of the animal-derived antibody. To this end, an antibody database, an assay of crystal structure, a molecule modeling technology, or the like is used. However, even when CDR of the animal-derived antibody are grafted on the optimized human antibody framework, an amino acid affecting antigen binding may still be present on a mouse antibody framework, so that the antigen binding may not be preserved. Accordingly, an additional antibody engineering technology for restoring antigen binding is necessary.

A c-Met humanized antibody is a humanized antibody from which immunogenicity of c-Met mouse antibody is removed. For example, the c-Met humanized antibody may be an anti c-Met humanized antibody that includes a heavy chain variable region having an amino acid sequence set forth in SEQ ID NO: 2 and a light chain variable region having an amino acid sequence set forth in SEQ ID NO: 7, an anti c-Met humanized antibody that includes a heavy chain variable region having an amino acid sequence set forth in SEQ ID NO: 2 and a light chain variable region having an amino acid sequence set forth in SEQ ID NO: 9, or an anti c-Met humanized antibody that includes a heavy chain variable region having an amino acid sequence set forth in SEQ ID NO: 5 and a light chain variable region having an amino acid sequence set forth in SEQ ID NO: 7.

According to an embodiment of the present invention, the c-Met humanized antibody may be a monoclonal antibody.

A whole antibody includes two full-length light chains and two full-length heavy chains, wherein the light chains may respectively bind to the heavy chains by a disulfide bond. An antibody includes a constant region which is divided into a heavy chain constant region and a light chain constant region. The heavy chain constant region has gamma ($\gamma$), mu ($\mu$), alpha ($\alpha$), delta ($\delta$), and epsilon ($\epsilon$) types, and as a subclass, has gamma 1 ($\gamma$1), gamma 2 ($\gamma$2), gamma 3 ($\gamma$3), gamma 4 ($\gamma$4), alpha 1 ($\alpha$1), and alpha 2 ($\alpha$2). The light chain constant region has kappa ($\kappa$) and lambda ($\lambda$) types.

The term "heavy chain" may be interpreted as including a full length heavy chain that includes a variable region domain $V_H$ having an amino acid sequence sufficient to impose specificity to an antigen, three constant region domains ($C_{H1}$, $C_{H2}$, and $C_{H3}$), and a hinge. Also, the term "light chain" is interpreted as including a full length light chain that includes a variable region domain $V_L$ having an amino acid sequence sufficient to impose specificity to an antigen, and a constant region domain ($C_L$).

The term "complementarity determining regions (CDR)" refers to amino acid sequences of hypervariable regions of a heavy chain and a light chain immunoglobulin. A heavy chain and a light chain may each have three CDRs (CDRH1, CDRH2, CDRH3 and CDRL1, CDRL2, CDRL3). A CDR may provide a major contact residue when an antibody binds to an antigen or epitope. Also, the term "specifically binding" or "specifically recognized" are the same as typically known to one of ordinary skill in the art, and refer to an immunization reaction due to a specific interaction between an antigen and an antibody.

According to an embodiment of the present invention, the antibody may be an antigen binding fragment selected from the group consisting of scFv, (scFv)$_2$, Fab, Fab', and F(ab')$_2$.

The term "antigen binding fragment" refers to a fragment of a whole immunoglobulin structure, that is, a portion of polypeptide to which an antigen binds. For example, the antigen binding fragment may be scFv, (scFv)$_2$, Fab, Fab', or F(ab')$_2$, but is not limited thereto. For example, Fab includes light chain and heavy chain variable regions, a light chain constant region, and a first heavy chain constant region ($C_{H1}$), and thus, has one antigen binding site. Fab' is different from Fab in the presence of a hinge region on which one or more cysteine residues are included at a C-terminus of a heavy chain $C_{H1}$ domain. F(ab')$_2$ antibody is formed by binding of the cysteine residues to the hinge region via a disulfide bond. Fv is a minimum antibody fragment having only a heavy chain variable region and a light chain variable region. A recombination technology for producing the Fv fragment is widely known in the art. A two-chain Fv has a heavy chain variable region and a light chain variable region which are linked to each other by a non-covalent bond, and a single-chain Fv has a heavy chain variable region and a light-chain variable region which are linked to each other via, in general, a peptide linker, or which are directly linked to a C-terminus to form a dimer structure like the two-chain Fv. The antigen binding fragment may be obtained by using a protein hydrolysis enzyme (for example, if a whole antibody is restriction-cleaved by using papain, Fab may be obtained, and if cleaved by using pepsin, a F(ab')$_2$ fragment may be obtained) and a generic recombination technology.

Another aspect of the present invention provides a polynucleotide that encodes a heavy chain variable region of an anti c-Met humanized antibody which is selected from amino acid sequences set forth in SEQ ID NO: 1 to SEQ ID NO: 5.

Another aspect of the present invention provides a polynucleotide that encodes a light chain variable region of an anti c-Met humanized antibody which is selected from amino acid sequences set forth in SEQ ID NO: 6 to SEQ ID NO: 9.

The term "polynucleotide" is a polymer of dioxyribo nucleotide or ribo nucleotide existing in a single-stranded or double-stranded form. The term "polynucleotide" includes an RNA genome sequence, DNA (gDNA and cDNA), and an RNA sequence transcripted therefrom, and also includes an analog of a natural polynucleotide unless defined otherwise.

The polynucleotide may further include, in addition to the polynucleotide sequence for encoding an amino acid sequence of a heavy chain variable region or a light chain variable region of the antibody that specifically binds to c-Met protein, a sequence that is complementary thereto. The complementary sequence may be a completely complementary sequence or a substantially complementary sequence, and may be, for example, a sequence that may be hybridized with a nucleotide sequence that encodes an amino acid sequence of a heavy chain variable region or a light chain variable region of an antibody that specifically binds to the c-Met protein under stringent conditions.

Also, the nucleotide sequence for encoding an amino acid sequence of a heavy chain variable region or a light chain variable region may be varied. The sequence varying includes addition or depletion of a nucleotide, non-conservative substitution, or conservative substitution. The polynucleotide for encoding an amino acid sequence of a heavy chain variable region or a light chain variable region of an antibody that specifically binds to c-Met protein may be interpreted as including a nucleotide sequence that shows substantial identity to the polynucleotide sequence. The substantial identity may refer to a sequence that shows, for example, at least 80% homology, at least 90% homology, at least 95% homology, at least 98% homology, or at least 99% homology when an arbitrary other sequence and the nucleotide sequence are aligned, and then the aligned sequence is assayed by using an algorithm that is typically used in the art.

Another aspect of the present invention provides a recombinant vector including: the polynucleotide that encodes a heavy chain variable region of an anti c-Met humanized antibody which is selected from amino acid sequences set forth in SEQ ID NO: 1 to SEQ ID NO: 5; and a promoter that is operatively linked to the polynucleotide.

Another aspect of the present invention provides a recombinant vector including: the polynucleotide that encodes a light chain variable region of an anti c-Met humanized antibody which is selected from amino acid sequences set forth in SEQ ID NO: 6 to SEQ ID NO: 9; and a promoter that is operatively linked to the polynucleotide.

The term "vector" refers to a means for expressing a target gene in a host cell. This term includes, for example, a plasmid vector, a cozmid vector, or a bacteriophage vector, and an adeno-related virus vector, such as an adenovirus vector, or a retrovirus vector. As the recombinant vector, a publicly available plasmid (for example, pSC101, pGV1106, pACYC177, ColE1, pKT230, pME290, pBR322, pUC8/9, pUC6, pBD9, pHC79, pIJ61, pLAFR1, pHV14, pGEX series, pET series, pUC19, etc), a phage (for example, λgt4λB, λ-Charon, λΔz1, M13, etc.), or a virus (for example, SV40, etc) may be used after manipulation.

In the recombinant vector, the polynucleotide for encoding an amino acid sequence of a heavy chain variable region and a light chain variable region may be operatively linked to the promoter. The term "operatively linked" indicates a functional linking between a nucleotide expression regulation sequence (for example, promoter sequence) and other nucleotide sequences. Accordingly, due to the operative linking, the regulation sequence may regulate transcription and/or translation of other nucleotide sequences.

The recombinant vector may be either a typical vector for cloning or a vector for expression. As the expression vector, vectors that are typically used to express a foreign protein in plants, animals, or microorganisms in the art may be used. The recombinant vector may be constructed by using various known methods.

The recombinant vector may be constructed using prokaryotic cells or eukaroytic cells as a host. For example, if an expression vector is used and prokaryotic cells are used as a host, in general, the vector may include a strong promoter for proceeding transcription (for example, pL$^\lambda$ promoter, trp promoter, lac promoter, tac promoter, T7 promoter, etc.), a ribosome binding site for the initiation of translation, and a transcription/translation termination sequence. If eukaroytic cells are used as a host, a replication origin that operates in eukaroytic cells included in a vector may be a f1 replication origin, a SV40 replication origin, a pMB1 replication origin, an adeno replication origin, an AAV replication origin, a BBV replication origin, or the like, but is not limited thereto. Also, a promoter derived from a genome of a mammal cells (for example, a metalothionine promoter) or a promoter derived from a mammal virus (for example, an adenovirus post promoter, a vaccinia virus 7.5K promoter, a SV40 promoter, a cytomegalo virus promoter, and a tk promoter of HSV) may be used, and a transcroption termination sequence may be, in general, a polyadenylated sequence.

Also, a vector for expressing the heavy chain variable region and the light chain variable region of the antibody may be a vector system in which the heavy chain variable region and the light chain variable region are simultaneously expressed in single vector, or a vector system in which the heavy chain variable region and the light chain variable region are expressed in different vectors. In the latter case, the two vectors may be introduced into a host cell through co-transformation and targeted-transformation.

Another aspect of the present invention provides a pharmaceutical composition for the prevention or treatment of cancer, wherein the pharmaceutical composition includes an anti c-Met humanized antibody including a heavy chain variable region that is selected from amino acid sequences set forth in SEQ ID NO: 1 to SEQ ID NO: 5 and a light chain variable region that is selected from amino acid sequences set forth in SEQ ID NO: 6 to SEQ ID NO: 9; and a pharmaceutically acceptable support, a diluent, or an excipient.

According to an embodiment of the present invention, the antibody may be an anti c-Met humanized antibody that includes a heavy chain variable region having an amino acid sequence set forth in SEQ ID NO: 2 and a light chain variable region having an amino acid sequence set forth in SEQ ID NO: 7, an anti c-Met humanized antibody that includes a heavy chain variable region having an amino acid sequence set forth in SEQ ID NO: 2 and a light chain variable region having an amino acid sequence set forth in SEQ ID NO: 9, or an anti c-Met humanized antibody that includes a heavy chain variable region having an amino acid sequence set forth in SEQ ID NO: 5 and a light chain variable region having an amino acid sequence set forth in SEQ ID NO: 7.

According to an embodiment of the present invention, the cancer may be selected from squamous cell carcinoma, small cell lung cancer, non-small cell lung cancer, adenocarcinoma of lung, squamous cell carcinoma of lung, peritonitis, skin cancer, intracutaneous or intraocular melanoma, rectal cancer, anal region cancer, esophageal cancer, small bowel neoplasm, endocrine glands cancer, parathyroid cancer, adrenal gland cancer, soft tissue sarcoma, urethral adenocarcinoma, chronic/acute leukemia, lymphocytic lymphoma, hepatocellular carcinoma, gastric cancer, pancreatic cancer, glioblastoma, cervical cancer, ovarian cancer, hepatoma, bladder cancer, hepatic tumor, breast cancer, colon carcinoma, colorectal cancer, endometrial/uterine cancer, salivary gland tumor, renal carcinoma, prostate cancer, prostate cancer, vulva cancer/cancer of the vulva, thyroid cancer, liver cancer, and head and neck cancer. The pharmaceutical composition may include a pharmaceutically acceptable support. The pharmaceutically acceptable support included in the pharmaceutical composition may be any one of various supports that are typically used in preparing formulations, and may be, for example, lactose, dextrose, sucrose, sorbitol, mannitol, starch, acasia rubber, starch, alginate, gelatin, calcium silicate, microcrystalline cellulose, polyvinyl pyrrolidone, cellulose, water, syrup, methyl cellulose, methylhydroxybenzoate, propylhydroxylbenzoate, talc, magnesium stearate, or mineral oil, is not limited thereto. The pharmaceutical composition may additionally include a lubricant, a wetting agent, a sweetener, a favoring agent, an emulsifier, a suspension agent, a preserving agent, or the like.

The pharmaceutical composition for the prevention or treatment of cancer may be administered orally or non-orally. When the composition is administered non-orally, intravenous injection, subcutaneous injection, intramuscular injection, intraperitoneal injection, intracutaneous injection, topical administration, intranasal administration, intrapulmonary administration, intrarectal administration, or the like may be used. When the composition is administered orally, the oral composition needs to be formulated such that its active ingredients are coated or formulated for the protection from decomposition in the stomach because protein or peptide is digested. Also, the composition may be administered via any device that may allow active ingredients to home to a target cell.

The pharmaceutically effective amount of the pharmaceutical composition for the prevention or treatment of cancer may vary according to a formulation method, an administration method, the age, body weight, gender, or morbid state of a patient, food, an administration time, an administration pathway, an excretion speed, or reaction sensitivity. A dosage of the composition may be in a range of about 0.001 to about 100 mg/kg based on an adult. The term "pharmaceutical effective amount" may indicate an amount that is sufficient to prevent or treat cancer, or to prevent or treat a disease caused by neovasculogenesis.

The composition may be formulated in a unit dosage form by using a method that is obvious to one of ordinary skill in the art and a pharmaceutically acceptable support and/or excipient, or may be manufactured by using a multi-dosage container. In this case, the formulation may be a solution, suspension, syrup, or emulsion in an oil or aqueous medium, an extract, powder, a granule, a tablet, or a capsule, and a dispersant or a stabilizer may be further included in the composition. Also, the composition may be administered as an individual therapeutic agent, or co-administered with other therapeutic agents, and in the latter case, the administration may be sequentially or simultaneously performed with other therapeutic agents. Also, the composition may be formulated as immuno liposome due to the inclusion of an antibody or an antigen binding fragment. A liposome including an antibody may be produced by using various known methods. The immuno liposome is a lipid composition that includes phosphatidylcolin, cholesterol, and polyethyleneglycol-derived phosphatidylethanol amine, and may be produced by reverse-phase evaporation. For example, Fab' fragment of an antibody may be grafted on a liposome through a disulfide-exchange reaction. A chemical therapeutic agent, such as doxorubicin, may be additionally included in a liposome.

According to an embodiment of the present invention, the antibody may act as an antagonist of the c-Met protein.

The term "antagonist" is interpreted as including incomplete or complete blocking, suppression, or neutralizing one or more biological activities of a target (for example, c-Met). For example, an "antagonist" antibody refers to an antibody that suppresses or reduces biological activities of an antigen (for example, c-Met) to which the antibody binds. The antagonist may, due to the binding of a receptor to a ligand, reduce phosphorylation of the receptor, or may incapacitate or kill cells that are activated by a ligand. Also, the antagonist may completely block an interaction between a receptor and a ligand, or may substantially reduce the interaction by three-dimensional structure change of receptor or down regulation.

One or more embodiments will now be described in detail with reference to examples. However, the present invention is not limited to the one or more embodiments.

EXAMPLE 1

Production of c-Met Mouse Antibody AbF46

(1) Immunization of Mouse

To obtain a mouse for development of a hybridoma cell strain, 4 to 6-week old five BALB/c mice (Japan SLC, Inc.) were each administered a mixture of 100 μg of human c-Met/Fc fusion protein (R&D Systems) and an equivalent amount of complete Freund's adjuvant by intraperitoneal injection. 2 weeks later, an antigen (in an amount half the previously injected amount) was mixed with incomplete Freund's adjuvant by using the same method as described above, and the mixture was intraperitoneally injected into the mice. One week later, a final boosting was performed thereon, and 3 days later, blood was collected from tails of the mice to obtain serum, following by dilution with PBS at $\frac{1}{1000}$. Then, an increase of an antibody that recognizes c-Met was confirmed with ELISA. A mouse from which a sufficient amount of the antibody was obtained was chosen from the mice and then a cell fusion process was performed thereon.

(2) Cell Fusion and Hybridoma Production

Three days before cell fusion, a mixture including 50 μg of PBS and human c-Met/Fc fusion protein was intraperitoneally injected into a mouse, and then the immunized mouse was anesthetized and a spleen located in the left-hand of the mouse body was removed. The obtained spleen was ground by using a mesh to isolate cells, followed by mixing with a culture medium (DMEM) to prepare a spleen cell suspension. The suspension was centrifuged to collect a cell layer. $1 \times 10^8$ of the obtained spleen cells and $1 \times 10^8$ of myeloma cells (Sp2/0) were mixed and centrifuged to precipitate cells. The precipitate was slowly dispersed, followed by treatment with 45% polyethylene glycol (PEG)(1 ml) contained in a culture medium (DMEM), and the result was maintained at a temperature of 37° C. for 1 minute, followed by addition of 1 ml of the culture medium (DMEM). Thereafter, 10 ml of the culture medium (DMEM) was added thereto for 1 minute, and the result was left in water at a temperature of 37° C. for 5 minutes, and then, the total amount was adjusted to be 50 ml and centrifuged. The cell precipitate was re-suspended in a separation medium (HAT medium) to a level of about 1 to $2 \times 10^5$/ml, and 0.1 ml thereof was distributed to each well of a 96-well plate and cultured in a carbon dioxide incubator at a temperature of 37° C.

(3) Screening of Hybridoma Cells Producing Monoclonal Antibody with Respect to c-Met Protein Hybridoma cells that specifically reacted to the c-Met protein were screened from among the hybridoma cell group prepared according to Example 2 above by using a human c-Met/Fc fusion protein and a human Fc protein as antigen.

50 µl (2 ug/ml) of the human c-Met/Fc fusion protein was loaded onto each well of a microtiter plate to attach the protein on the surface of the plate, and non-reacted antigen was removed by washing. To screen out and remove an antibody that binds to Fc, not the c-Met, a human Fc protein was attached to the plate surface in the same manner as described above. 50 ul of a hybridoma cell culture was loaded onto each well and reacted for 1 hour, followed by sufficiently washing with a phosphate buffer solution-between 20 (TBST) solution to remove non-reacted culture solution. Then, a goat anti-mouse IgG-horseradish peroxidase was added thereto for reaction at room temperature for one hour, followed by sufficient washing with a TBST solution. Then, a substrate solution (OPD) of peroxidase was added thereto for reaction, and a degree of the reaction was measured by using an ELISA Reader at a wavelength of 450 nm to repeatedly screen hybridoma cell strains secreting an antibody that had a strong biding force specifically to only the human c-Met protein, not the human Fc. The hybridoma cell strain obtained through repeated screening was subjected to limiting dilution to finally obtain one clone of a hybridoma cell line that generates a monoclonal antibody. The finally screened monoclonal antibody production hybridoma was donated to a Korean cell strain bank (Cancer Research Institute, Seoul National University, College of Medicine, 28 Yongon-dong, Chongno-gu, Seoul, 110-744, Korea on Oct. 9, 2009, and received accession number KCLRF-BP-00220.

(4) Production and Purification of Monoclonal Antibody

The hybridoma cells prepared according to Example 3 were cultured in a serum-free medium, and a monoclonal antibody was produced from the culture solution, followed by purification.

First, the hybridoma cells cultured in 50 ml of a 10% FBS-containing culture medium (DMEM) were centrifuged and the cell precipitate was washed twice or more with 20 ml of PBS to remove FBS, and in this state, 50 ml of culture medium (DMEM) was re-suspended in the cell precipitate, followed by culturing for 3 days at a temperature of 37° C. in a carbon dioxide incubator. Thereafter, cells producing antibody were removed by centrifuging, and a culture solution including secreted antibodies was isolated and preserved at a temperature of 4° C., or directly collected and an antibody was pure-purified from 50 ml to 300 ml of the culture solution by using an AKTA purification device (GE Health) equipped with an affinity column (Protein G agarose column; Pharmacia, USA), followed by substitution of an supernatant with PBS by using a protein agglomeration filter (Amicon), and a purified antibody was preserved and used in the following experiments.

EXAMPLE 2

Production of Chimeric Antibody chAbF46 with Respect to c-Met

When a mouse antibody is injected into a human for therapeutic purposes, immunogenicity is highly likely to occur. Thus, to solve this problem, a chimeric antibody chAbF46 was manufactured from the mouse antibody AbF46 manufactured according to Example 1 by substituting a constant region of the mouse antibody AbF46, not a variable region that is associated to an antigen binding, with a sequence of human IgG1 antibody.

A gene was synthesized such that a sequence corresponding to a heavy chain was designed to have 'EcoRI-signal sequence-VH-NheI-CH-TGA-XhoI' (SEQ ID NO: 7), and a sequence corresponding to a light chain was designed to have 'EcoRI-signal sequence-VL-BsiWI-CL-TGA-XhoI' (SEQ ID NO: 8). Thereafter, a DNA fragment having a sequence corresponding to the heavy chain (SEQ ID NO: 7) and a DNA fragment having a sequence corresponding to the light chain (SEQ ID NO: 8) were respectively cloned in a pOptiVEC™-TOPO TA Cloning Kit and a pcDNA™ 3.3-TOPO TA Cloning Kit (Cat no. 8300-01), both included in an OptiCHO™ Antibody Express Kit (Cat no. 12762-019) manufactured by Invitrogen Company, while EcoRI (NEB, R0101S) and XhoI (NEB, R0146S) were respectively used as restriction enzymes, thereby constructing vectors for expressing a chimeric antibody.

The constructed vectors were each amplified by using a Qiagen Maxiprep kit (Cat no. 12662), and 293T cells ($2.5 \times 10^7$) were transfected with a ratio of 4:1 (80 µg:20 µg) of the heavy chain-containing vector and the light chain-containing vector in 360 µl of 2M $CaCl_2$. Then, the cells were incubated in a 10% FBS-supplemented DMEM medium at a temperature of 37° C., under 5% $CO_2$ for 5 hours, and then, incubated in a FBS-free DMEM medium for 48 hours at a temperature of 37° C. under 5% $CO_2$.

The cultured cells were centrifuged to collect 100 ml of the supernatant, followed by purification using AKTA Prime (GE health care). Protein A column (GE health care, 17-0405-03) was installed on an AKTA Prime, and then the culture solution was supplied thereto at a flow rate of 5 ml/min, and elution was performed thereon using a IgG elution buffer (Thermo Scientific, 21004). This was replaced with a PBS buffer to finally purify a chimeric antibody AbF46 (hereinafter referred to as chAbF46).

EXAMPLE 3

Production of Deimmunized Humanized Antibody huAbF46 from Chimeric Antibody chAbF46

First, an amino acid sequence of a variable region of an AbF46 mouse antibody was assayed by using Swiss PDB to determine a sequence that plays an important role in recognizing an antigen. The assay results showed that a sequence of a framework region of the AbF46 mouse antibody was similar to a sequence of a human antibody, and a major sequence of CDR and a sequence of the framework region were each divided into about 10 segments and each segment constituted various variants. An iTope™ technology (Perry, L. C. A, Jones, T. D. and Baker, M. P., New Approaches to Prediction of Immune Responses to Therapeutic Proteins during Preclinical Development (2008), Drugs RD 9 (6): 385-396) which allowed peptides binding to human MHC class II to be identified from these variants on in-silico phase, and TCED™ database were used, and a sequence of humanized antibody was screened by using a method in which a T-cell epitope associated with the sequence was removed (Bryson, C. J., Jones, T. D. and Baker, M. P. Prediction of Immunogenicity of Therapeutic Proteins (2010). Biodrugs 24 (1):1-8). The segments obtained as described above were subjected to composite humanization to design five sequences $V_H$ and four sequences $V_L$, and humanized antibodies having a total of 20 sequences of a combination of the designed $V_H$ and $V_L$.

Five amino acid sequences (AT-VH1, AT-VH2, AT-VH3, AT-VH4, and AT-VH5) of a heavy chain variable region designed by the deimmunizing method were represented by SEQ ID NO: 1 to SEQ ID NO: 5 and all of these were designed to belong to a VH3 family which is known as the most stable sequence among heavy chain sequences of IgG1 antibody.

Four amino acid sequences (AT-Vk1, AT-Vk2, AT-Vk3, and AT-Vk4) of a light chain variable region designed by the deimmunizing method were represented by SEQ ID NO: 6 to SEQ ID NO: 9, and all of these were designed to belong to a Vk1 family which is known as the most stable sequence among light chain sequences of IgG1 antibody.

Figure 1:
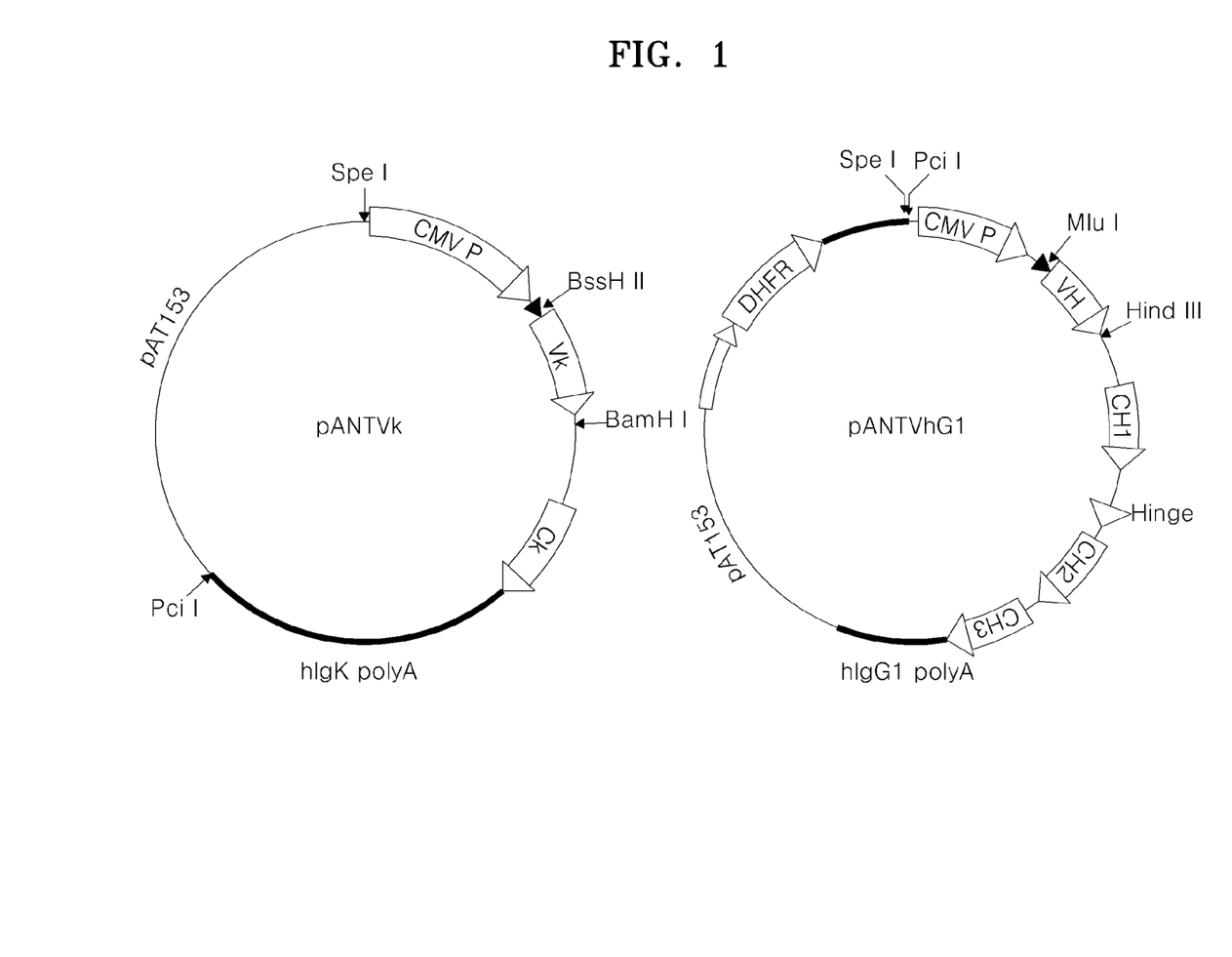
FIG. 1 is a map of a vector for expressing an anti c-Met humanized antibody according to an embodiment of the present invention.

Polynucleotides of the designed heavy chain variable regions and light chain variable regions were commissioned to and synthesized by Antitpoe Company and the synthesized polynucleotides were cloned on a pANT expression vector (Antitpoe Company, England). The polynucleotides of the heavy chain regions were inserted into an 'MluI-HindIII' restriction enzyme region, and the polynucleotides of the light chain regions were inserted into 'BssHII-BamHI' restriction enzyme region. Maps of vectors (pANTVhG1 and pANTVk) in which the heavy chain regions and the light chain regions were cloned are illustrated in FIG. 1, and sequences of the synthesized polynucleotides were set forth in SEQ ID NO: 10 to SEQ ID NO: 18.

HEK293 cells ($2.5 \times 10^7$) were transfected with a ratio of 4:1 (80 ug:20 μg) of the heavy chain-containing vector and the light chain-containing vector in 360 μl of 2M $CaCl_2$. Thereafter, the cells were incubated in a 10% FBS-supplemented DMEM medium at a temperature of 37° C., under 5% $CO_2$ for 5 hours, and then, incubated in a FBS-free DMEM medium for 72 hours at a temperature of 37° C. under 5% $CO_2$.

Figure 2:
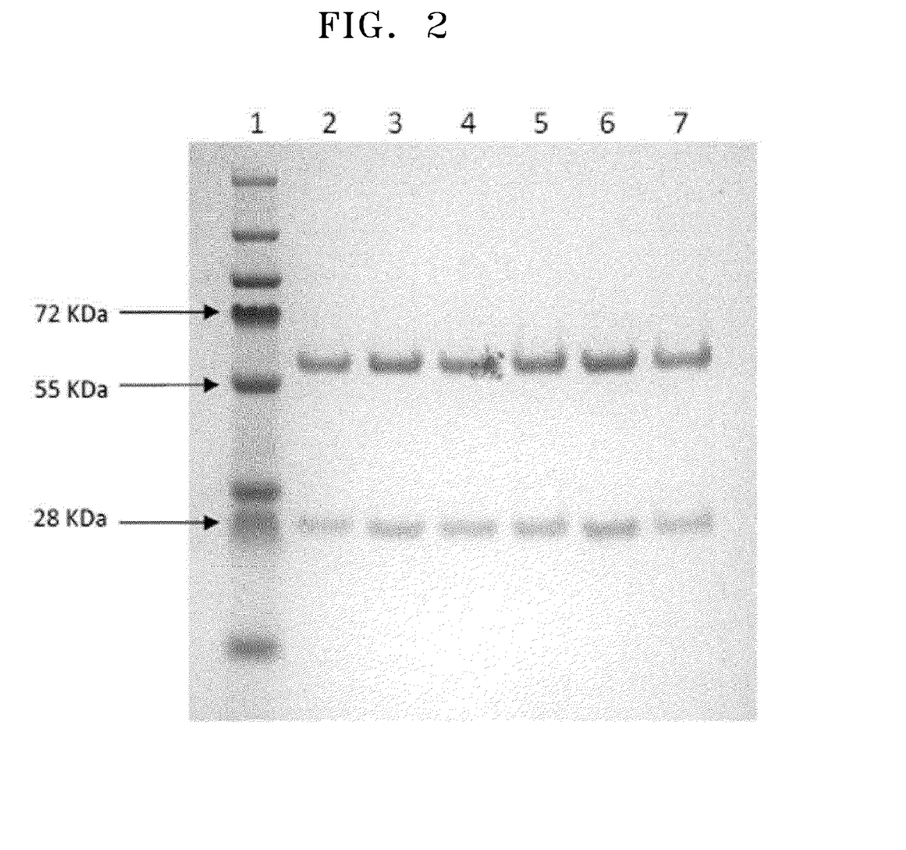
FIG. 2 is a SDS-PAGE gel picture showing purification results of an anti c-Met humanized antibody according to an embodiment of the present invention. Lane 1 indicates Prestained MW Markers (Fermentas PageRuler Cat. No. SM1811), lane 2 indicates chAbF46, lane 3 indicates an antibody including a combination of AT-VH2 and AT-Vk2, lane 4 indicates an antibody including a combination of AT-VH2 and AT-Vk4, lane 5 indicates an antibody including a combination of AT-VH4 and AT-Vk4, lane 6 indicates an antibody including a combination of AT-VH5 and AT-Vk2, and lane 7 indicates an antibody including a combination of AT-VH5 and AT-Vk4.

The cultured cells were centrifuged and a 100 ml of supernatant was obtained. Then antibodies were purified from the supernatants by using AKTA Prime (GE healthcare). AKTA Prime was equipped with Protein A column (GE healthcare, 17-0405-03) and a culture solution was supplied thereinto at a flow rate of 5 ml/min, followed by elution using an IgG elution buffer (Thermo Scientific, 21004). This was replaced with a PBS buffer to, finally, purify 20 deimmunized humanized antibodies. FIG. 2 shows results of some of the purified antibodies. In FIG. 2, lane 1 indicates Prestained MW Markers (Fermentas PageRuler Cat. No. SM1811), lane 2 indicates chAbF46, lane 3 indicates an antibody including a combination of AT-VH2 and AT-Vk2, lane 4 indicates an antibody including a combination of AT-VH2 and AT-Vk4, lane 5 indicates an antibody including a combination of AT-VH4 and AT-Vk4, lane 6 indicates an antibody including a combination of AT-VH5 and AT-Vk2, and lane 7 indicates an antibody including a combination of AT-VH5 and AT-Vk4. These samples were subjected to electrophoresis by using NuPage4-12% Bis-Tris gel (Invitrogen Cat. No. NP032BOX) for 35 minutes at 250V.

EXAMPLE 4

Confirmation of c-Met Antigen Binding Ability of Deimmunized Humanized Antibody huAbF46

The c-Met antigen proving the ability of the humanized antibody manufactured as described above was confirmed by comparing with chimeric antibody chAbF46 according to a competition ELISA method The antigens were coated by overnight incubation at a temperature of 4° C. using Nunc Immuno MaxiSort 96 well flat bottom microtiter plate (Fisher Cat. No. DIS-971-030J) and 1.0 μg/ml and 100 μl/well of c-Met/Fc chimera (R&D Systems Cat. No. 358-MT/CF). chAbF46 and 20 humanized antibodies were diluted and at a concentration of 10 μg/ml to 0.078 μg/ml, they were mixed with biotinylated chAbF46 (0.1 μg/ml, final conc.), followed by incubation at a temperature of 37° C. for 2 hours. The amount of biotinylated chAbF46 antibody binding to the antigen was measured using streptavidin-HRP (Sigma cat. No S5512) and an OPD substrate (Sigma Cat. No. P9187), and IC50 data were calculated from the results and the data are shown in Table 1 below (all units in nM).

TABLE 1

| Heavy chain | light chain | | | |
|---|---|---|---|---|
| | AT-Vk1 | AT-Vk2 | AT-Vk3 | AT-Vk4 |
| AT-VH1 | 1.48 | 1.49 | 2.30 | 1.51 |
| AT-VH2 | 2.30 | 1.28 | 1.69 | 1.37 |
| AT-VH3 | 3.53 | 4.50 | 5.51 | 1.81 |
| AT-VH4 | 2.40 | 3.13 | 1.99 | 1.41 |
| AT-VH5 | 2.04 | 1.46 | 1.57 | 1.62 |

EXAMPLE 5

Affinity Assay of Deimmunized Humanized Antibody huAbF46

Affinity of three antibodies having high IC50 data (an antibody having a combination of AT-VH2 and AT-Vk2, an antibody having a combination of AT-VH2 and AT-Vk4, and an antibody having a combination of AT-VH5 and AT-Vk2), from among the deimmunized humanized antibodies manufactured as descried above, with respect to the c-Met antigen were measured by using Biacore (GE healthcare). The respective antibodies were immobilized on a CM5 chip at about 80~110 RU, and then the human c-Met protein antigen was injected at nine different concentrations within a concentration range of 100 nM to 0.39 nM at a speed of 30 μl/min, and $k_{on}$ values and $k_{off}$ values were calculated and $K_D$ values were calculated therefrom, and results thereof are shown in Table 2 below. The chimeric antibody chAbF46 had about 4.27 nM of binding force with respect to the c-Met antigen, and the three deimmunized humanized antibodies had a binding force of 4.68 nM to 5.75 nM (Table 2). From the results, it was confirmed that the deimmunized humanized antibodies had a similar level of binding force with respect to the c-Met antigen, compared to the chimeric antibody chAbF46 without a decrease in a binding force.

TABLE 2

| Antibody | kon (1/Ms) | koff (1/s) | KD (nM) |
|---|---|---|---|
| chAbF46 | $5.86 \times 10^5$ | $2.50 \times 10^{-4}$ | 4.27 |
| chAbF46-U6-MC7 | $5.38 \times 10^5$ | $2.52 \times 10^{-4}$ | 4.68 |
| chAbF46-U3-HC9 | $5.88 \times 10^5$ | $3.38 \times 10^{-4}$ | 5.75 |
| chAbF46-U6-HC8 | $8.34 \times 10^5$ | $4.36 \times 10^{-4}$ | 5.23 |

EXAMPLE 6

CDR Sequence of Deimmunized Humanized Antibody huAbF46

Amino acid sequences of the heavy chain and light chain CDR of the humanized antibody huAbF46 are shown in Table 3.

TABLE 3

| | CDR1 | CDR2 | CDR3 |
|---|---|---|---|
| AbF46 heavy chain CDR sequence | DYYMS (SEQ ID NO: 19) | FIRNKANGYTTEYS ASVKG (SEQ ID NO: 20) | DNWFAY (SEQ ID NO: 21) |
| AbF46 light chain CDR sequence | KSSQSLLASGN QNNYLA (SEQ ID NO: 22) | WASTRVS (SEQ ID NO: 23) | QQSYSAPLT (SEQ ID NO: 24) |

Anti c-Met humanized antibodies according to the above embodiments have high affinity to c-Met and are deimmunized, and thus, effectively prevent or treat cancer.

It should be understood that the exemplary embodiments described herein should be considered in a descriptive sense only and not for purposes of limitation. Descriptions of features or aspects within each embodiment should typically be considered as available for other similar features or aspects in other embodiments.

EXAMPLE 7

Immunogenicity of Chimeric Antibody chAbF46 and Humanized Antibody huAbF46 from which Immunogenicity is Removed Immunogenicity of chimeric antibody chAbF46 and humanized antibody huAbF46 from which immunogenicity is removed was confirmed with a healthy donor T cell proliferation response. As a control, Herceptin®, Phytohaemagglutin (PHA), and Keyhole limpet hemocyanin (KLH) were used. Peripheral blood mononuclear cells (PBMC) obtained from blood of donors were cultured at $4 \times 10^6$ to $6 \times 10^6$ cells per well with 0.3 μM test antibody in 0.5 ml of AIM-V® media on a 24-well plate for 5 days to 8 days, and then, the respective cells were divided into three aliquots, each having a volume of 100 μl, and the aliquots were transferred onto a 96-well plate. 0.75 μCi [$^3$H]-thymidine isotope (Perkin Elmer®, Beaconsfield, UK) was added to AIM-V® media. After 18 hours, an amount (counts per minute; cpm) of the isotope incorporated into the cells was measured to calculate a proliferation rate of cells.

In Table 4, P indicates a positive T cell responses for proliferation during entire time course of 5 to 8 days, and P* indicates a borderline of T cell responses for proliferation. A frequency of positive T cell responses for proliferation assay is indicated as a proliferation rate (%) in Table 4. A positive donor response was defined as SI≥2.00, significance p<0.05 (including borderline responses) for one or more time points during the time course assay. The number of days when a response was measured as a threshold value or more is not considered, and the number of donors of which a positive proliferation response was induced was counted at multiple time points. Regarding donor 37, KLH data was not able to be obtained (N/D; not determined).

TABLE 4

| Donor | chAbF46 (chimeric antibody) | huAbF46 (humanized antibody) | Herceptin | PHA | KLH |
|---|---|---|---|---|---|
| donor 1 | | | | P | P |
| donor 2 | | | | P | P |
| donor 2 | | | | P | P |
| donor 3 | | | | P | P |
| donor 4 | | | | P | P |
| donor 5 | | P | | P | P |
| donor 6 | | | | P | P |
| donor 7 | | | | P | P |
| donor 8 | | | | P | P |
| donor 9 | | | | P | P |
| donor 10 | | | | P | P |
| donor 11 | | | | P | P |
| donor 12 | | | | P | P |
| donor 13 | | | | P | |
| donor 14 | | | | P | P |
| donor 15 | | | | P | |
| donor 16 | | | | P | P |
| donor 17 | | | | P | P |
| donor 18 | P | | P | P | P |
| donor 19 | | | | P | P |
| donor 20 | | | | P | P |
| donor 21 | P | | P | P | P |
| donor 22 | | | | P | P |
| donor 23 | P | | | P | P |
| donor 24 | | | | P | P |
| donor 25 | | | | P | P |
| donor 26 | | | | P | P |
| donor 27 | | | | P | P |
| donor 28 | | | | P | P |
| donor 29 | | P | | P | P |
| donor 30 | | | | P | P |
| donor 31 | | | | P | P |
| donor 32 | | | | P | P |
| donor 33 | | | | P | P |
| donor 34 | | | | P | P |
| donor 35 | | | | P | P |
| donor 36 | | | | P | P |
| donor 37 | | | | P | N/D |
| donor 38 | | | | P | |
| donor 39 | | | | P | P |
| donor 40 | | | | P | P |
| donor 41 | | | | P | P |
| donor 42 | P | | | P | P |
| donor 43 | | | | P | P |
| donor 44 | | | | P | P |
| donor 45 | | | | P | |
| donor 46 | | | | P | P |
| donor 47 | | | | P | P |
| donor 48 | | | | P | P |
| donor 49 | | | | P | P |
| donor 50 | | | | P | P |
| Proliferation rate (%) | 8 | 2 | 6 | 100 | 90 |

Proliferation assay data shows that positive (SI≥2.00, p<0.05 including borderline responses) T cell responses were detected against all test antibodies in a proportion of the donor. Table 4 shows summarized results of positive responses against test antibodies (P; positive reaction). All donors showed positive T cell responses against PHA in the proliferation assay, and cells in the ex vivo cultures were functional (data not shown). In addition, a frequency of positive T cell responses against control antibody (Herceptin®) was in a range of 0 to 6%, and a frequency of positive T cell reaction with respect to KLH, which is a reproducibility control, was in a range of 85% to 95%.

An antibody from which immunogenicity is removed induced a lower frequency in T cell proliferation response. In addition, the antibody from which immunogenicity is removed, compared to a chimeric antibody, induced a low mean magnitude of the positive T cell proliferation response (Table 5). The antibody from which immunogenicity is removed shows lower immunogenicity than control antibody Herceptin of which mean SI is 2.40 and a frequency of response is 6%.

TABLE 5

| Antibody | Mean SI | Standard derivation SI | Frequency of response (%) |
|---|---|---|---|
| chAbF46 (chimeric antibody) | 2.20 | 0.35 | 8 |
| huAbF46 (humanized antibody) | 2.12 | N/A | 2 |
| Herceptin | 2.40 | 0.36 | 6 |
| KLH | 5.91 | 5.06 | 90 |

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. An anti c-Met humanized antibody comprising a heavy chain variable region comprising any one of SEQ ID NOs: 1-5, and a light chain variable region comprising any one of SEQ ID NOs: 6-9.

2. The anti c-Met humanized antibody of claim 1, wherein the heavy chain variable region comprises SEQ ID NO: 2 and the light chain variable region comprises SEQ ID NO: 7.

3. The anti c-Met humanized antibody of claim 1, wherein the heavy chain variable region comprising SEQ ID NO: 2, and the light chain variable region comprises SEQ ID NO: 9.

4. The anti c-Met humanized antibody of claim 1, wherein the heavy chain variable region comprises SEQ ID NO: 5 and the light chain variable region comprises SEQ ID NO: 7.

5. The anti c-Met humanized antibody of claim 1, wherein the antibody specifically binds c-Met from a human or monkey, a mouse, or a rat.

6. The anti c-Met humanized antibody of claim 1, wherein the anti c-Met humanized antibody is a monoclonal antibody.

7. The anti c-Met humanized antibody of claim 1, wherein the anti c-Met humanized antibody is less immunogenic than trastuzumab.

8. The anti c-Met humanized antibody of claim 1, wherein the anti c-Met humanized antibody is an antigen binding fragment selected from the group consisting of scFv, (scFv)$_2$, Fab, Fab' and F(ab')$_2$.

9. A pharmaceutical composition comprising an anti c-Met humanized antibody of claim 1 and a pharmaceutically acceptable support, diluent, or excipient.

10. The pharmaceutical composition of claim 9, wherein the anti c-Met humanized antibody comprises a heavy chain variable region comprising SEQ ID NO: 2 and a light chain variable region comprising SEQ ID NO: 7.

11. The pharmaceutical composition of claim 9, wherein the anti c-Met humanized antibody comprises a heavy chain variable region comprising SEQ ID NO: 2 and a light chain variable region comprising SEQ ID NO: 9.

12. The pharmaceutical composition of claim 9, wherein the anti c-Met humanized antibody comprises a heavy chain variable region comprising SEQ ID NO: 5 and a light chain variable region comprising SEQ ID NO: 7.

* * * * *

SEQUENCE LISTING

<160> NUMBER OF SEQ ID NOS: 24

<210> SEQ ID NO 1
<211> LENGTH: 117
<212> TYPE: PRT
<213> ORGANISM: Artificial Sequence
<220> FEATURE:
<223> OTHER INFORMATION: Synthetic (AT-VH1)

<400> SEQUENCE: 1

Glu Val Lys Leu Val Glu Ser Gly Gly Gly Leu Val Gln Pro Gly Gly
1               5                   10                  15

Ser Leu Arg Leu Ser Cys Ala Thr Ser Gly Phe Thr Phe Thr Asp Tyr
            20                  25                  30

Tyr Met Ser Trp Val Arg Gln Pro Pro Gly Lys Gly Leu Glu Trp Leu
        35                  40                  45

Gly Phe Ile Arg Asn Lys Ala Asn Gly Tyr Thr Thr Glu Tyr Ser Ala
    50                  55                  60

Ser Val Lys Gly Arg Phe Thr Ile Ser Arg Asp Asn Ser Lys Ser Thr
65                  70                  75                  80

Leu Tyr Leu Gln Met Asn Ser Leu Arg Ala Glu Asp Ser Ala Thr Tyr
                85                  90                  95

Tyr Cys Ala Arg Asp Asn Trp Phe Ala Tyr Trp Gly Gln Gly Thr Leu
            100                 105                 110

Val Thr Val Ser Ser
        115

```
<210> SEQ ID NO 2
<211> LENGTH: 117
<212> TYPE: PRT
<213> ORGANISM: Artificial Sequence
<220> FEATURE:
<223> OTHER INFORMATION: Synthetic (AT-VH2)

<400> SEQUENCE: 2

Glu Val Lys Leu Val Glu Ser Gly Gly Gly Leu Val Gln Pro Gly Gly
1               5                   10                  15

Ser Leu Arg Leu Ser Cys Ala Thr Ser Gly Phe Thr Phe Thr Asp Tyr
            20                  25                  30

Tyr Met Ser Trp Val Arg Gln Pro Pro Gly Lys Gly Leu Glu Trp Leu
        35                  40                  45

Gly Phe Ile Arg Asn Lys Ala Asn Gly Tyr Thr Thr Glu Tyr Ser Ala
    50                  55                  60

Ser Val Lys Gly Arg Phe Thr Ile Ser Arg Asp Asn Ser Lys Ser Thr
65                  70                  75                  80

Leu Tyr Leu Gln Met Asn Ser Leu Arg Ala Glu Asp Thr Ala Thr Tyr
                85                  90                  95

Tyr Cys Ala Arg Asp Asn Trp Phe Ala Tyr Trp Gly Gln Gly Thr Leu
            100                 105                 110

Val Thr Val Ser Ser
        115

<210> SEQ ID NO 3
<211> LENGTH: 117
<212> TYPE: PRT
<213> ORGANISM: Artificial Sequence
<220> FEATURE:
<223> OTHER INFORMATION: Synthetic (AT-VH3)

<400> SEQUENCE: 3

Glu Val Gln Leu Val Glu Ser Gly Gly Gly Leu Val Gln Pro Gly Gly
1               5                   10                  15

Ser Leu Arg Leu Ser Cys Ala Thr Ser Gly Phe Thr Phe Thr Asp Tyr
            20                  25                  30

Tyr Met Ser Trp Val Arg Gln Pro Pro Gly Lys Gly Leu Glu Trp Leu
        35                  40                  45

Gly Phe Ile Arg Asn Lys Ala Asn Gly Tyr Thr Thr Glu Tyr Ser Ala
    50                  55                  60

Ser Val Lys Gly Arg Phe Thr Ile Ser Arg Asp Asn Ser Lys Ser Thr
65                  70                  75                  80

Leu Tyr Leu Gln Met Asn Ser Leu Arg Ala Glu Asp Thr Ala Thr Tyr
                85                  90                  95

Tyr Cys Ala Arg Asp Asn Trp Phe Ala Tyr Trp Gly Gln Gly Thr Leu
            100                 105                 110

Val Thr Val Ser Ser
        115

<210> SEQ ID NO 4
<211> LENGTH: 117
<212> TYPE: PRT
<213> ORGANISM: Artificial Sequence
<220> FEATURE:
<223> OTHER INFORMATION: Synthetic (AT-VH4)

<400> SEQUENCE: 4
```

-continued

Glu Val Gln Leu Val Glu Ser Gly Gly Gly Leu Val Gln Pro Gly Gly
1               5                   10                  15

Ser Leu Arg Leu Ser Cys Ala Thr Ser Gly Phe Thr Phe Thr Asp Tyr
            20                  25                  30

Tyr Met Ser Trp Val Arg Gln Pro Pro Gly Lys Gly Leu Glu Trp Leu
        35                  40                  45

Gly Phe Ile Arg Asn Lys Ala Asn Gly Tyr Thr Thr Glu Tyr Ser Ala
    50                  55                  60

Ser Val Lys Gly Arg Phe Thr Ile Ser Arg Asp Asn Ser Lys Asn Thr
65                  70                  75                  80

Leu Tyr Leu Gln Met Asn Ser Leu Arg Ala Glu Asp Thr Ala Thr Tyr
                85                  90                  95

Tyr Cys Ala Arg Asp Asn Trp Phe Ala Tyr Trp Gly Gln Gly Thr Leu
            100                 105                 110

Val Thr Val Ser Ser
        115

<210> SEQ ID NO 5
<211> LENGTH: 117
<212> TYPE: PRT
<213> ORGANISM: Artificial Sequence
<220> FEATURE:
<223> OTHER INFORMATION: Synthetic (AT-VH5)

<400> SEQUENCE: 5

Glu Val Gln Leu Val Glu Ser Gly Gly Gly Leu Val Gln Pro Gly Gly
1               5                   10                  15

Ser Leu Arg Leu Ser Cys Ala Thr Ser Gly Phe Thr Phe Thr Asp Tyr
            20                  25                  30

Tyr Met Ser Trp Val Arg Gln Pro Pro Gly Lys Gly Leu Glu Trp Leu
        35                  40                  45

Gly Phe Ile Arg Asn Lys Ala Asn Gly Tyr Thr Thr Glu Tyr Ser Ala
    50                  55                  60

Ser Val Lys Gly Arg Phe Thr Ile Ser Arg Asp Asn Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Ala Arg Asp Asn Trp Phe Ala Tyr Trp Gly Gln Gly Thr Leu
            100                 105                 110

Val Thr Val Ser Ser
        115

<210> SEQ ID NO 6
<211> LENGTH: 113
<212> TYPE: PRT
<213> ORGANISM: Artificial Sequence
<220> FEATURE:
<223> OTHER INFORMATION: Synthetic (AT-Vk1)

<400> SEQUENCE: 6

Asp Ile Leu Met Thr Gln Ser Pro Ser Ser Leu Thr Ala Ser Val Gly
1               5                   10                  15

Asp Arg Val Thr Met Thr Cys Lys Ser Ser Gln Ser Leu Leu Ala Ser
            20                  25                  30

Gly Asn Gln Asn Asn Tyr Leu Ala Trp His Gln Gln Lys Pro Gly Lys
        35                  40                  45

Ala Pro Lys Met Leu Ile Ile Trp Ala Ser Thr Arg Val Ser Gly Val
    50                  55                  60

```
Pro Asp Arg Phe Ile Gly Ser Gly Ser Gly Thr Asp Phe Thr Leu Thr
 65                  70                  75                  80

Ile Ser Ser Leu Gln Ala Glu Asp Val Ala Val Tyr Tyr Cys Gln Gln
                 85                  90                  95

Ser Tyr Ser Ala Pro Leu Thr Phe Gly Gln Gly Thr Lys Leu Glu Ile
            100                 105                 110

Lys
```

<210> SEQ ID NO 7
<211> LENGTH: 113
<212> TYPE: PRT
<213> ORGANISM: Artificial Sequence
<220> FEATURE:
<223> OTHER INFORMATION: Synthetic (AT-Vk2)

<400> SEQUENCE: 7

```
Asp Ile Leu Met Thr Gln Ser Pro Ser Ser Leu Ser Ala Ser Val Gly
 1               5                  10                  15

Asp Arg Val Thr Ile Thr Cys Lys Ser Ser Gln Ser Leu Leu Ala Ser
                 20                  25                  30

Gly Asn Gln Asn Asn Tyr Leu Ala Trp His Gln Lys Pro Gly Lys
             35                  40                  45

Ala Pro Lys Met Leu Ile Ile Trp Ala Ser Thr Arg Val Ser Gly Val
     50                  55                  60

Pro Asp Arg Phe Ile Gly Ser Gly Ser Gly Thr Asp Phe Thr Leu Thr
 65                  70                  75                  80

Ile Ser Ser Leu Gln Ala Glu Asp Val Ala Val Tyr Tyr Cys Gln Gln
                 85                  90                  95

Ser Tyr Ser Ala Pro Leu Thr Phe Gly Gln Gly Thr Lys Leu Glu Ile
            100                 105                 110

Lys
```

<210> SEQ ID NO 8
<211> LENGTH: 113
<212> TYPE: PRT
<213> ORGANISM: Artificial Sequence
<220> FEATURE:
<223> OTHER INFORMATION: Synthetic (AT-Vk3)

<400> SEQUENCE: 8

```
Asp Ile Gln Met Thr Gln Ser Pro Ser Ser Leu Ser Ala Ser Val Gly
 1               5                  10                  15

Asp Arg Val Thr Ile Thr Cys Lys Ser Ser Gln Ser Leu Leu Ala Ser
                 20                  25                  30

Gly Asn Gln Asn Asn Tyr Leu Ala Trp His Gln Lys Pro Gly Lys
             35                  40                  45

Ala Pro Lys Met Leu Ile Ile Trp Ala Ser Thr Arg Val Ser Gly Val
     50                  55                  60

Pro Asp Arg Phe Ile Gly Ser Gly Ser Gly Thr Asp Phe Thr Leu Thr
 65                  70                  75                  80

Ile Ser Ser Leu Gln Ala Glu Asp Val Ala Val Tyr Tyr Cys Gln Gln
                 85                  90                  95

Ser Tyr Ser Ala Pro Leu Thr Phe Gly Gln Gly Thr Lys Leu Glu Ile
            100                 105                 110

Lys
```

<210> SEQ ID NO 9
<211> LENGTH: 113
<212> TYPE: PRT
<213> ORGANISM: Artificial Sequence
<220> FEATURE:
<223> OTHER INFORMATION: Synthetic (AT-Vk4)

<400> SEQUENCE: 9

Asp Ile Gln Met Thr Gln Ser Pro Ser Ser Leu Ser Ala Ser Val Gly
1               5                   10                  15

Asp Arg Val Thr Ile Thr Cys Lys Ser Ser Gln Ser Leu Leu Ala Ser
            20                  25                  30

Gly Asn Gln Asn Asn Tyr Leu Ala Trp His Gln Gln Lys Pro Gly Lys
        35                  40                  45

Ala Pro Lys Met Leu Ile Ile Trp Ala Ser Thr Arg Val Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Ser Tyr Ser Ala Pro Leu Thr Phe Gly Gln Gly Thr Lys Leu Glu Ile
            100                 105                 110

Lys

<210> SEQ ID NO 10
<211> LENGTH: 375
<212> TYPE: DNA
<213> ORGANISM: Artificial Sequence
<220> FEATURE:
<223> OTHER INFORMATION: Synthetic (nucleotide sequence of AT-VH1)

<400> SEQUENCE: 10
acgcgtgtcc actccgaagt gaagctggtg aaagcggcg gaggcctggt gcagcctggc     60
ggcagcctga ctgagctg cgccaccagc ggcttcacct tcaccgacta ctacatgagc    120
tgggtgcgcc agccccctgg caagggactg gaatggctgg gcttcatccg gaacaaggcc    180
aacggctaca ccaccgagta cagcgccagc gtgaagggcc ggttcaccat cagccgggac    240
aacagcaaga gcagcctgta cctgcagatg aacagcctgc gggccgagga ctccgccacc    300
tactactgcg ccagagacaa ttggttcgcc tactggggcc agggcaccct ggtgacagtg    360
tccagcggta agctt                                                     375

<210> SEQ ID NO 11
<211> LENGTH: 375
<212> TYPE: DNA
<213> ORGANISM: Artificial Sequence
<220> FEATURE:
<223> OTHER INFORMATION: Synthetic (nucleotide sequence of AT-VH2)

<400> SEQUENCE: 11
acgcgtgtcc actccgaagt gaagctggtg aaagcggcg gaggcctggt gcagcctggc     60
ggcagcctga ctgagctg cgccaccagc ggcttcacct tcaccgacta ctacatgagc    120
tgggtgcgcc agccccctgg caagggactg gaatggctgg gcttcatccg gaacaaggcc    180
aacggctaca ccaccgagta cagcgccagc gtgaagggcc ggttcaccat cagccgggac    240
aacagcaaga gcagcctgta cctgcagatg aacagcctgc gggccgagga caccgccacc    300
tactactgcg ccagagacaa ttggttcgcc tactggggcc agggcaccct ggtgacagtg    360
tccagcggta agctt                                                     375

<210> SEQ ID NO 12
<211> LENGTH: 375
<212> TYPE: DNA
<213> ORGANISM: Artificial Sequence
<220> FEATURE:
<223> OTHER INFORMATION: Synthetic (nucleotide sequence of AT-VH3)

<400> SEQUENCE: 12

| | |
|---|---|
| acgcgtgtcc actccgaggt gcagctggtg aaagcggcg gaggactggt gcagcctggc | 60 |
| ggcagcctga gactgagctg cgccaccagc ggcttcacct tcaccgacta ctacatgagc | 120 |
| tgggtgcgcc agccccctgg caagggactg aatggctgg gcttcatccg gaacaaggcc | 180 |
| aacggctaca ccaccgagta cagcgccagc gtgaagggcc ggttcaccat cagccgggac | 240 |
| aacagcaaga gcagcctgta cctgcagatg aacagcctgc gggccgagga caccgccacc | 300 |
| tactactgcg ccagagacaa ttggttcgcc tactggggcc agggcaccct ggtgacagtg | 360 |
| tccagcggta agctt | 375 |

<210> SEQ ID NO 13
<211> LENGTH: 375
<212> TYPE: DNA
<213> ORGANISM: Artificial Sequence
<220> FEATURE:
<223> OTHER INFORMATION: Synthetic (nucleotide sequence of AT-VH4)

<400> SEQUENCE: 13

| | |
|---|---|
| acgcgtgtcc actccgaggt gcagctggtg aaagcggcg gaggactggt gcagcctggc | 60 |
| ggcagcctga gactgagctg cgccaccagc ggcttcacct tcaccgacta ctacatgagc | 120 |
| tgggtgcgcc agccccctgg caagggactg aatggctgg gcttcatccg gaacaaggcc | 180 |
| aacggctaca ccaccgagta cagcgccagc gtgaagggcc ggttcaccat cagccgggac | 240 |
| aacagcaaga acagcctgta cctgcagatg aacagcctgc gggccgagga caccgccacc | 300 |
| tactactgcg ccagagacaa ttggttcgcc tactggggcc agggcaccct ggtgacagtg | 360 |
| tccagcggta agctt | 375 |

<210> SEQ ID NO 14
<211> LENGTH: 375
<212> TYPE: DNA
<213> ORGANISM: Artificial Sequence
<220> FEATURE:
<223> OTHER INFORMATION: Synthetic (nucleotide sequence of AT-VH5)

<400> SEQUENCE: 14

| | |
|---|---|
| acgcgtgtcc actccgaggt gcagctggtg aaagcggcg gaggactggt gcagcctggc | 60 |
| ggcagcctga gactgagctg cgccaccagc ggcttcacct tcaccgacta ctacatgagc | 120 |
| tgggtgcgcc agccccctgg caagggactg aatggctgg gcttcatccg gaacaaggcc | 180 |
| aacggctaca ccaccgagta cagcgccagc gtgaagggcc ggttcaccat cagccgggac | 240 |
| aacagcaaga acagcctgta cctgcagatg aacagcctgc gggccgagga caccgccgtg | 300 |
| tactactgcg ccagagacaa ttggttcgcc tactggggcc agggcaccct ggtgacagtg | 360 |
| tccagcggta agctt | 375 |

<210> SEQ ID NO 15
<211> LENGTH: 389
<212> TYPE: DNA
<213> ORGANISM: Artificial Sequence
<220> FEATURE:

<223> OTHER INFORMATION: Synthetic (nucleotide sequence of AT-Vk1)

<400> SEQUENCE: 15

```
gcgcgcgatg tgacatcgtg atgacccaga gccccagcag cctgaccgcc agcgtgggcg      60
acagagtgac catgacctgc aagagcagcc agtctctgct ggccagcggc aaccagaaca     120
actacctggc ctggcaccag cagaagcccg gcaaggcccc caagatgctg atcatctggg     180
ccagcaccag agtgtccggc gtgcccgata gattcatcgg cagcggctcc ggcaccgact     240
tcaccctgac catcagctct ctgcaggccg aggacgtggc cgtgtactac tgccagcaga     300
gctacagcgc ccctctgacc ttcggccagg gcaccaagct ggaaatcaag cgtgagtaga     360
atttaaactt tgcttcctca gttggatcc                                       389
```

<210> SEQ ID NO 16
<211> LENGTH: 389
<212> TYPE: DNA
<213> ORGANISM: Artificial Sequence
<220> FEATURE:
<223> OTHER INFORMATION: Synthetic (nucleotide sequence of AT-Vk2)

<400> SEQUENCE: 16

```
gcgcgcgatg tgacatcgtg atgacccaga gccccagcag cctgaccgcc agcgtgggcg      60
acagagtgac catcacatgc aagagcagcc agagcctgct ggctagcggc aaccagaaca     120
actacctggc ctggcaccag cagaagcccg gcaaggcccc caagatgctg atcatctggg     180
ccagcaccag agtgtccggc gtgcccgata gattcatcgg cagcggctcc ggcaccgact     240
tcaccctgac catcagctct ctgcaggccg aggacgtggc cgtgtactac tgccagcaga     300
gctacagcgc ccctctgacc ttcggccagg gcaccaagct ggaaatcaag cgtgagtaga     360
atttaaactt tgcttcctca gttggatcc                                       389
```

<210> SEQ ID NO 17
<211> LENGTH: 389
<212> TYPE: DNA
<213> ORGANISM: Artificial Sequence
<220> FEATURE:
<223> OTHER INFORMATION: Synthetic (nucleotide sequence of AT-Vk3)

<400> SEQUENCE: 17

```
gcgcgcgatg tgacatccag atgacccaga gccccagcag cctgagcgcc agcgtgggcg      60
acagagtgac catcacatgc aagagcagcc agagcctgct ggctagcggc aaccagaaca     120
actacctggc ctggcaccag cagaagcccg gcaaggcccc caagatgctg atcatctggg     180
ccagcaccag agtgtccggc gtgcccgata gattcatcgg cagcggctcc ggcaccgact     240
tcaccctgac catcagctct ctgcaggccg aggacgtggc cgtgtactac tgccagcaga     300
gctacagcgc ccctctgacc ttcggccagg gcaccaagct ggaaatcaag cgtgagtaga     360
atttaaactt tgcttcctca gttggatcc                                       389
```

<210> SEQ ID NO 18
<211> LENGTH: 389
<212> TYPE: DNA
<213> ORGANISM: Artificial Sequence
<220> FEATURE:
<223> OTHER INFORMATION: Synthetic (nucleotide sequence of AT-Vk4)

<400> SEQUENCE: 18

```
gcgcgcgatg tgacatccag atgacccaga gccccagcag cctgagcgcc agcgtgggcg      60
acagagtgac catcacatgc aagagcagcc agagcctgct ggctagcggc aaccagaaca     120
```

```
actacctggc ctggcaccag cagaagcccg gcaaggcccc caagatgctg atcatctggg    180
ccagcaccag agtgtccggc gtgccagata gattcagcgg cagcggctcc ggcaccgact    240
tcaccctgac catcagctct ctgcaggccg aggacgtggc cgtgtactac tgccagcaga    300
gctacagcgc ccctctgacc ttcggccagg gcaccaagct ggaaatcaag cgtgagtaga    360
atttaaactt tgcttcctca gttggatcc                                     389
```

```
<210> SEQ ID NO 19
<211> LENGTH: 5
<212> TYPE: PRT
<213> ORGANISM: Artificial Sequence
<220> FEATURE:
<223> OTHER INFORMATION: Synthetic (heavy chain CDR1 of AbF46)

<400> SEQUENCE: 19

Asp Tyr Tyr Met Ser
1               5

<210> SEQ ID NO 20
<211> LENGTH: 19
<212> TYPE: PRT
<213> ORGANISM: Artificial Sequence
<220> FEATURE:
<223> OTHER INFORMATION: Synthetic (heavy chain CDR2 of AbF46)

<400> SEQUENCE: 20

Phe Ile Arg Asn Lys Ala Asn Gly Tyr Thr Thr Glu Tyr Ser Ala Ser
1               5                   10                  15

Val Lys Gly

<210> SEQ ID NO 21
<211> LENGTH: 6
<212> TYPE: PRT
<213> ORGANISM: Artificial Sequence
<220> FEATURE:
<223> OTHER INFORMATION: Synthetic (heavy chain CDR3 of AbF46)

<400> SEQUENCE: 21

Asp Asn Trp Phe Ala Tyr
1               5

<210> SEQ ID NO 22
<211> LENGTH: 17
<212> TYPE: PRT
<213> ORGANISM: Artificial Sequence
<220> FEATURE:
<223> OTHER INFORMATION: Synthetic (light chain CDR1 of AbF46)

<400> SEQUENCE: 22

Lys Ser Ser Gln Ser Leu Leu Ala Ser Gly Asn Gln Asn Asn Tyr Leu
1               5                   10                  15

Ala

<210> SEQ ID NO 23
<211> LENGTH: 7
<212> TYPE: PRT
<213> ORGANISM: Artificial Sequence
<220> FEATURE:
<223> OTHER INFORMATION: Synthetic (light chain CDR2 of AbF46)

<400> SEQUENCE: 23

Trp Ala Ser Thr Arg Val Ser
1               5
```

```
<210> SEQ ID NO 24
<211> LENGTH: 9
<212> TYPE: PRT
<213> ORGANISM: Artificial Sequence
<220> FEATURE:
<223> OTHER INFORMATION: Synthetic (light chain CDR3 of AbF46)

<400> SEQUENCE: 24

Gln Gln Ser Tyr Ser Ala Pro Leu Thr
1               5
```